United States Patent [19]

Doecke et al.

[11] Patent Number: 5,142,038

[45] Date of Patent: Aug. 25, 1992

[54] PROCESS OF ENANTIOMERIC SEPARATION OF CARBACEPHEM INTERMEDIATES

[75] Inventors: Christopher W. Doecke, Greenwood; Jeffrey N. Levy, Lafayette; Wayne D. Luke, West Lafayette; Michael A. Staszak, Indianapolis, all of Ind.

[73] Assignee: Eli Lilly and Company, Indianapolis, Ind.

[21] Appl. No.: 734,394

[22] Filed: Jul. 23, 1991

[51] Int. Cl.$^5$ .................. C07D 205/085; C07B 57/00
[52] U.S. Cl. .................................................. 540/200
[58] Field of Search ........................................ 540/200

[56] References Cited

U.S. PATENT DOCUMENTS 4,708,956 11/1987 Hirata et al. ............... 514/210

OTHER PUBLICATIONS

C. C. Bodurow et al., *Tetrahedron Letters*, vol. 30, No. 19, pp. 2321-2324 (1989).

*Primary Examiner*—Mark L. Beach

*Attorney, Agent, or Firm*—Joseph A. Jones; Leroy Whitaker

[57] ABSTRACT

Enantiomerically pure $\beta$-lactam intermediates of the formula (I)

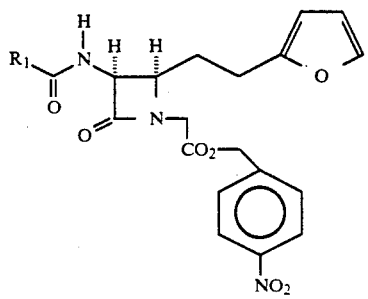

are isolated from a haloalkane solvent through precipitation with methyl-t-butyl ether or methanol. The products thus obtained are key intermediates in the synthesis of antibiotic aagents. The process is appropriate for large scale production.

12 Claims, No Drawings

PROCESS OF ENANTIOMERIC SEPARATION OF CARBACEPHEM INTERMEDIATES

BACKGROUND

1. Field of Invention

This invention belongs to the field of semi-synthetic organic chemistry, and provides an advantageous process for isolating certain carbacephem intemediates. This process provides the desired enantiomerically pure β-lactam compounds in high yield, as well as in high chemical purity through an economical and efficient isolation process.

2. State of the Art

An important clinical trial candidate, (6R, 7S)-7-(R)-phenylglycylamido-3-chloro-1-azabicyclo[4.2.0]-oct-2-ene-8-one-2-carboxylic acid (loracarbef), claimed in U.S. Pat. No. 4,708,956, may be synthesized by various routes. The known synthetic routes involve multiple, complex steps, necessitating efficient, high yielding steps to maximize the overall yield of loracarbef. An object of the present invention is to provide an efficient isolation method, suitable for large scale production, which will assure 100% enantiomeric purity as well as high yields of key β-lactam intermediates. Chemical enantiomeric isolation methods have been reported; however, the yields from the process are unacceptably low. C. C. Budurow, et. al., "An Enantioselective Synthesis of Loracarbef", 30 Tetrahedron Letters 2321 (1989). The improved isolation method of this invention assures 100% enantiomeric purity with yields greater than 95%.

SUMMARY OF THE INVENTION

This invention provides a process for isolating a β-lactam compound with about 100% enantiomeric purity, of the formula

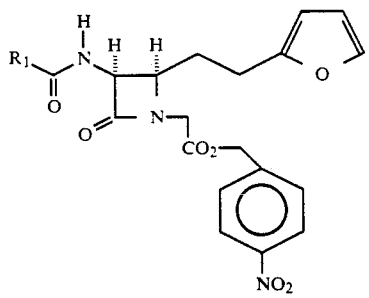

I wherein $R_1$ is $CH_3$, $t\text{-}C_4H_9$, $C_6H_5CH_2O$, $C_6H_5$, $C_6H_5OCH_2$ or $C_6H_5CH_2$; from a haloalkane solvent, comprising diluting the solution with methyl-t-butyl ether or methanol to precipitate the product.

DESCRIPTION OF THE PREFERRED EMBODIMENTS

The process of this invention isolates useful β-lactam compounds of about 100% enantiomeric purity. The isolation method is efficient and suitable for large scale production. The compounds isolated by this process are believed to be known in the art.

A preferred group of products include those wherein $R_1$ is $C_6H_5CH_2O$ or $C_6H_5OCH_2$. The most preferred product of this invention is cis-(+)-3-phenoxyacetamido-4-[2-(2-furanyl)ethyl]-2-oxo-1-azetidine acetic acid (4-nitrophenyl)methyl ester (hereinafter loracarbef intermediate). In the above process, the starting material may be obtained by methodology known in the β-lactam art. For example, see Preparation 1 and the method of Hatanaka, et al., 24 Tetrahedron Letters 4837 (1983).

In the above process, the term haloalkane solvent refers to a solvent having one or more chloro, bromo, or iodo substituents. The compound to be isolated must be soluble in the halogenated solvent and the halogenated solvent must be miscible with methyl-t-butyl ether and methanol. The miscibility tests necessary to select an appropriate haloalkane solvent can be readily carried out by one of ordinary skill in organic chemistry. Chloro solvents of appropriate solubility are preferred. The most preferred halogenated solvent is $CH_2Cl_2$.

The isolation process of this invention will be explained in detail. The process is an efficient means of chemically isolating key enantiomerically pure β-lactam intermediates. The process is appropriate for use in large-scale equipment, tolerant of a variety of β-lactams and produces acceptable yields of product.

The process of this invention efficiently removes reagents remaining in the starting material mixture from prior processes. This process will remove such impurities as phase transfer catalyst, undesired enantiomer and other residual impurities. The process of this invention is most effective when the starting material has an enantiomeric purity greater than 77%.

Isolation of the product from halogenated solvent and methyl-t-butyl ether or methanol may be achieved by conventional methods including chilling, solvent evaporation, and seeding. The most preferred method includes distillation of the $CH_2Cl_2$ to reduce the halogenated solvent volume, with simultaneous addition of the methanol or methyl-t-butyl ether to maintain a constant volume, or by refluxing the mixture. When an appropriate amount has been added, the mixture is allowed to slowly cool to ambient temperature.

The slurry may be cooled in an ice bath to enhance the crystallization yield. The solid may be isolated from the solvent by conventional methods including filtration and centrifugation. The isolated solid may be washed with methanol or methyl-t-butyl ether to enhance the purity of the product.

The isolated solid may be dried by conventional methods including air, vacuum and vacuum oven at about 25° C. to about 45° C. Alternatively, the wet cake may be used for subsequent reactions.

The compound of formula I may be subjected to ozonolysis to provide the corresponding 2-[2-(carboxy)-eth-1-yl] derivative, which can be derivatized to useful 1-carba(dethia) cemphems. The 4-carboxyazetidinone derivative may be converted to the corresponding 4-(2-phenoxycarbonyleth-1-yl) compound and subsequently cyclized to a 1-carba(dethia)-3-enol-3-cephem under Dieckman cyclization conditions. The resulting 1-carba(dethia)-3-enol-3-cephem intermediate may be chlorinated with triphenylphosphite dichloride using the method of Hatfield, U.S. Pat. No. 4,230,644, and acylated with an activated form of D-phenylglycine to provide the antibiotic loracarbef. See also, Bodurow et al., 30 Tetrahedron Letters 2321 (1989).

The following Examples are provided to further illustrate the invention. It is not intended that the invention be limited in scope by reason of any of the following Examples.

EXAMPLE 1

Large Scale Isolation using Methanol

A 640 l solution of methylene chloride and 77.5 Kg. of loracarbef intermediate was washed once with a 600 l volume of water. The methylene chloride solution was distilled, with simultaneous addition of methanol, at a rate of about 180 l/hr to maintain a constant volume. When the vapor temperature reached 60° C., and about 800 l of methanol had been added, the distillation was stopped. Immediately, the product began to crystallize. The slurry was cooled to about 180° C. over two hours, and then was stirred at about 18° C. for two additional hours. The crystalline product was filtered, washed with methanol, and dried in a rotary vacuum drier. Large product crystals of acceptable purity, particularly important for large scale handling, resulted from the isolation process. Product identity was confirmed by H.P.L.C. analysis, as described below.

Yield: 74.7 Kg. (96.2%)
Potency: 99.85%
Related substances: 0.31%
Enantiomeric purity: 100%
Filtration time: 4.0 minutes
H.P.L.C. retention time: 950 seconds The process of Example 1 was repeated with 74.4 Kg of starting loracarbef intermediate and the following results were obtained.

Yield: 72.7 Kg. (97.7%)
Potency: 100%
Related substances: 0.65%
Enantiomeric purity: 100%
Filtration time: 7.0 minutes

H.P.L.C. Chromatographic Assay for Enantiomeric Excess a. Standard Preparation

A 25 mg sample of the racemic mixture standard material was dissolved in 5 ml of methylene chloride and diluted to 50 ml with the diluent solution (preparation of diluent solution below).

b. Sample Preparation

A 25 mg sample of product was dissolved in 5 ml of methylene chloride and diluted to 50 ml with diluent solution.

c. Solution Preparation

1. Weak eluent: hexane
2. Strong eluent: isopropyl alcohol
3. Diluent solution: mixture of 550 ml of isopropyl alcohol and 450 ml of hexane to make a 55/45 (v/v) solution.

d. Sample Analysis

H.P.L.C. system with variable wave length U.V. detection system was assembled as follows:
1. Wave length: 270 mm
2. Flow rate: 1.5 ml/min
3. Injection volume: 10 microliters
4. Analytical column: 25 cm×4.6 mm I.D. Chiralcel OD from Diacel Chemical Industries, 5 micron packing
5. Column temperature: ambient
6. Isocratic mobile phase: 55/45 (strong eluent/weak eluent, may be premixed)

A 10 microliter sample of standard solution (prepared above) was injected onto the column. The retention time of the desired enantiomer should be between 800 and 950 seconds. The retention time of the inactive enantiomer should be between 600 and 750 seconds. The peak resolution should be at least 1.5.

A 10 microliter sample of standard solution was injected onto the column and the chromatogram was recorded. The sample loop was rinsed with diluent solution after injection of the standard and prior to injection of the sample. The rinse is required to prevent any carry over of standard solution into the sample injections. After the sample loop was rinsed, a 10 microliter sample of the product was injected and the chromatogram was recorded. The peak areas in the chromatogram were measured using an integrating device.

e. Data Analysis

In order to determine the percent of enantiomeric excess (% ee) from the areas of the peaks in the chromatograms, the following equation was utilized:

$$\frac{A-B}{A+B} \times 100 = \% \ ee$$

where:

A = the area of the (+)-isomer or 3S4R isomer in the sample.
B = the area of the (−)-isomer or 3R4S isomer in the sample.

PREPARATION 1

Preparation of β-Lactam Intermediates for Isolation Process

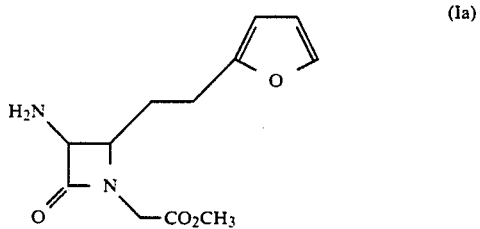

In the following process, the racemic mixture (Ia), denoted as the substrate for the reaction, can be obtained by methodology known in the β-lactam art. For example, a 2+2 cycloaddition reaction as set forth in scheme 1 may be utilized:

Scheme 1

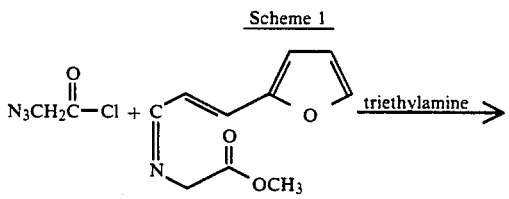

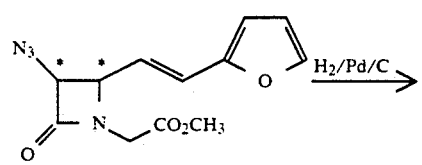

-continued
Scheme 1

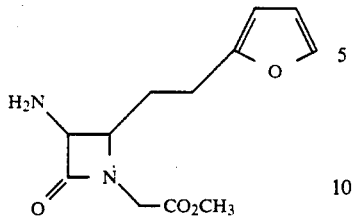

a. Acylation

A 40.0 g. sample of β-lactam formula Ia, with an enantiomeric purity of 89.5%, was placed in a 500 ml. five neck flask. The flask was fitted with an overhead stirring attachment, thermometer, addition funnel, a powder funnel and pH probe. A 150 ml. volume of water was added with stirring. The initial pH was 3.90. A 100 ml. volume of methylene chloride was added. The pH was 4.5 after the methylene chloride addition. The mixture was cooled to about 10° C. and 30.5 g. of sodium carbonate was added to the mixture. The pH of the mixture after the sodium carbonate addition was 7.4. The mixture was returned to ambient temperature while adding 14.6 ml. of phenoxyacetyl chloride dropwise over about 15 minutes. The pH of the mixture was about 7.8 after the addition of the phenoxyacetyl chloride.

The mixture was transferred to a separatory funnel and the methylene chloride layer was removed and saved. The aqueous layer was washed with 100 ml. of methylene chloride and the methylene chloride layer was collected. The two methylene chloride fractions were combined and washed with 100 ml. of water, 100 ml. of 5% sodium carbonate, and 100 ml. of brine. The methylene chloride layer was dried over magnesium sulfate, and filtered.

b. Hydrolysis

A three neck flask was fitted with an overhead stirrer, distillation head, and thermometer. The reaction vessel was heated to about 42° C. and a 150 ml. volume of water was added with stirring. The remaining methylene chloride was distilled away and the reaction vessel temperature jumped to about 52° C. The heating element was removed and a 150 ml volume of acetone was added. The mixture was cooled to about 15° C. and 21.74 ml. of 5N. sodium hydroxide were added dropwise over about 15 minutes. The mixture was allowed to stir at 15° C. for one hour. The distillation head was equipped with a vacuum adaptor and the reaction vessel was placed in a 25° C. warm water bath. Vacuum was applied to the reaction vessel to remove the acetone and methanol. The reaction vessel temperature was maintained at 25° C. When the water layer of the reaction mixture appeared to begin distilling, the vacuum and heat were removed. The remaining volume was 187 ml.

c. Esterification

The 187 ml. mixture was diluted to 200 ml. with methylene chloride. A 23.48 g. sample of p-nitrobenzyl bromide, 3.34 g. of tetrabutyl ammonium bromide and 200 ml. of methylene chloride were added to the organic mixture. The mixture was rapidly stirred overnight at ambient conditions. At noon the following day, the mixture was transferred to a separatory funnel for layer separation. The aqueous layer was extracted with 150 ml. of methylene chloride. The organic layers were combined and washed with 150 ml. of water, two 150 ml. volumes of 5% sodium carbonate, 150 ml. of 1N. hydrochloric acid, and 150 ml. of brine. The organic layer was collected and transferred to a 2 l. flask which was fitted with an overhead stirring apparatus and distillation head.

EXAMPLE 2

Laboratory Scale Isolation using Methyl-t-butyl ether

The resulting organic layer of Preparation 1 was diluted to a total volume of 500 ml. with methylene chloride. The organic layer was heated to boiling and 200 ml. of methylene chloride were distilled away. The distillation head was replaced with a reflux condenser. The mixture was heated to reflux, with stirring, and 200 ml. of methyl-t-butyl ether were added. The heating element was removed and the stirring mixture was allowed to cool to ambient temperature. Upon reaching ambient temperature, the reaction vessel was placed in an ice bath and allowed to stir for 30 minutes. The resulting solid was filtered and washed with 100 ml. of ice cold methyl-t-butyl ether. The solid was washed with 250 ml. of pentane. The solid was placed in a vacuum oven to dry at about 45° C.

Yield: 43.28 g. for the process of Preparation 1 and the isolation (82.7% overall yield).
Enantiomeric Purity: 100%
Related Substances: No phase transfer catalyst, no p-nitro benzyl bromide contamination.

We claim:

1. The process for isolating a β-lactam compound with about 100% enantiomeric purity, of the formula

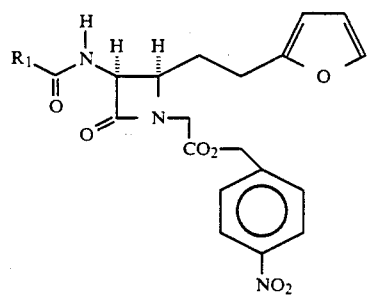

wherein $R_1$ is $CH_3$, $t-C_4H_9$, $C_6H_5CH_2O$, $C_6H_5$, $C_6H_5OCH_2$ or $C_6H_5CH_2$; from a haloalkane solvent, comprising diluting the solution with methyl-t-butyl ether or methanol to precipitate the product.

2. The process of claim 1, wherein $R_1$ is $C_6H_5CH_2O$ or $C_6H_5OCH_2$.

3. The process of claim 1, wherein $R_1$ is $C_6H_5OCH_2$.

4. The process of claim 1, wherein the haloalkane solvent is a chloro solvent.

5. The process of claim 2, wherein the haloalkane solvent is $C_1$ to $C_3$ chloroalkane.

6. The process of claim 2, wherein the haloalkane solvent is methylene chloride.

7. The process of claim 1, wherein the solution is diluted with methyl-t-butyl ether.

8. The process of claim 2, wherein the solution is diluted with methyl-t-butyl ether.

9. The process of claim 6, wherein the solution is diluted with methyl-t-butyl ether.

10. The process of claim 1, wherein the solution is diluted with methanol.

11. The process of claim 5, wherein the solution is diluted with methanol.

12. The process of claim 6, wherein the solution is diluted with methanol.

* * * * *